United States Patent [19]

Henderson

[11] Patent Number: 5,326,560
[45] Date of Patent: Jul. 5, 1994

[54] INSECTICIDE CARRIERS AND INSECTICIDES

[76] Inventor: Jack A. Henderson, 1609 Stanford, NE., Albuquerque, N. Mex. 87106-3729

[21] Appl. No.: 51,008

[22] Filed: Apr. 20, 1993

Related U.S. Application Data

[63] Continuation of Ser. No. 687,726, Apr. 18, 1991, abandoned.

[51] Int. Cl.$^5$ .............. A01N 63/00; A01N 65/00; A01N 25/08
[52] U.S. Cl. .............. 424/93 L; 514/65; 514/67; 514/770; 514/789
[58] Field of Search .............. 514/65, 122, 479, 770, 514/67, 789; 424/93

[56] References Cited

U.S. PATENT DOCUMENTS

| | | | |
|---|---|---|---|
| 3,888,903 | 6/1975 | Chupp | 260/468 E |
| 3,906,104 | 9/1975 | Partos | 424/303 |
| 3,962,356 | 6/1976 | Holan | 260/649 R |
| 4,058,607 | 11/1977 | Hennart et al. | 424/219 |
| 4,104,376 | 8/1978 | Zeck | 424/216 |
| 4,321,258 | 3/1982 | Dunlap | 514/770 |
| 4,334,910 | 6/1982 | Lörincz et al. | 504/123 |
| 4,361,436 | 11/1982 | McCarthy et al. | 71/86 |
| 4,389,401 | 6/1983 | Smolanoff | 424/248.56 |
| 4,424,214 | 1/1984 | Okada et al. | 424/200 |
| 4,455,308 | 6/1984 | Smolanoff | 424/248.57 |
| 4,564,639 | 1/1986 | Nagase et al. | 514/594 |
| 4,594,360 | 6/1986 | Coats | 514/716 |
| 4,632,938 | 12/1986 | Nagase et al. | 514/594 |
| 4,663,346 | 5/1987 | Coulston et al. | 514/456 |
| 4,740,505 | 4/1988 | Kamei et al. | 514/85 |
| 4,843,100 | 6/1989 | Nagase et al. | 514/594 |
| 4,869,896 | 9/1989 | Coulston et al. | 424/45 |

FOREIGN PATENT DOCUMENTS 1294868 10/1962 France .

OTHER PUBLICATIONS

Meyer, C. A. vol. 77 (1972) 77:168601k.
Nakamoto et al., CA 112:177223, 1990, "Insecticidal effects of a kieselgahr product . . . ".
Ross, CA 95:19491u, 1981, "Diatomaceous Earth as a Possible alternative to Chemical Insecticides".
Nelzina et al., CA 97: 105579b, 1982, "Mineral Dusts as Possible Insecticides. . . ".
Worthing et al., The Pesticide Manual, British Crop Protection Council, Eighth Edition, Lavenham Press Ltd. Lavenham, Eng. 1987.

*Primary Examiner*—Richard L. Raymond
*Assistant Examiner*—Brian G. Bembenick

[57] ABSTRACT

An insecticide carrier and insecticide comprising a mixture of petrolatum and diatomaceous earth. A diluent, such as crop oil, may be added to the mixture, particularly for use as a spray insecticide. Any of a variety of insecticides containing active ingredients may also be added. The resulting formulation provides a longer life product, as well as ultraviolet shielding, good adhesion to insects and vegetation, and increased insect penetration.

7 Claims, No Drawings

INSECTICIDE CARRIERS AND INSECTICIDES

This is a continuation of copending application(s) Ser. No. 07/687,726 filed on Apr. 18, 1991, (now abandoned).

BACKGROUND OF THE INVENTION

1. Field of the Invention (Technical Field)

This invention relates to carriers or insecticides, insecticides, and methods of making and using the carriers and insecticides.

2. Background Art

Today's emphasis on environmental protection requires careful selection and application of herbicides and pesticides. Specifically, ideal application of insecticides to crops, for example, would involve minimal quantities of insecticides effective over a longer period of time. Many insecticides, for example, pyrethrum, the pyrethroids, organophosphates, and biologicals rapidly degrade after exposure to ultraviolet radiation, hydrolysis and oxidation. This degradation of active insecticides may occur well before they have accomplished their purpose.

Insecticide carriers, often termed "extenders," are frequently mentioned in the prior art. U.S. Pat. No. 3,888,903, to Chupp, entitled *Phenyl-N-(1-alkenyl)-N-Methylcarbamates;* U.S. Pat. No. 3,906,104, to Partos, entitled *Insecticidal Sulfonates;* U.S. Pat. No. 3,962,356, to Holan, entitled *Substituted Cyclopropanes;* U.S. Pat. No. 4,361,436, to McCarthy, et al., entitled *Composition for Plant Growth Regulation;* U.S. Pat. No. 4,389,401, to Smolanoff, entitled *Arthropod Repellents;* U.S. Pat. No. 4,424,214, to Okada, et al., entitled *Insecticidal Pyrazolyl Phosphates;* and U.S. Pat. No. 4,455,308, to Smolanoff, entitled *Arthropod Repellents;* are exemplary of the employment of inert extenders combined with various specific active insecticides or herbicides. Among such extenders are disclosed petrolatum as a semi-solid extender, and diatomaceous earth (kieselguhr) as a solid extender. Significantly, however, the petrolatum and diatomaceous earth are not disclosed in combination.

Likewise, the following patents also disclose the separate use of diatomaceous earth and petrolatum as extenders, but not in combination:

U.S. Pat. No. 4,564,639, to Nagase, et al., entitled *N-(2,6-Difluorobenzoyl-N-'-(2-Fluoro-4-Halophenyl) Urea;* U.S. Pat. No. 4,594,360, to Coats, entitled *Chloronitroalkane Insecticides;* U.S. Pat. No. 4,632,938, to Nagase, et al., entitled *Thiophenylureas, Their Production and Use;* U.S. Pat. No. 4,663,346, to Coulston, et al., entitled *Insect Repellent;* U.S. Pat. No. 4,740,505, to Kamei, et al., entitled *Pyridazinyloxy (or Thio) Phenyl Phosphates;* U.S. Pat. No. 4,843,100, to Nagase, et al., entitled *Benzoylureas, Their Production and Use;* and U.S. Pat. No. 4,869,896, to Coulston, et al., entitled *Potentiated Insect Repellent Composition and Method.*

SUMMARY OF THE INVENTION
(DISCLOSURE OF THE INVENTION)

The present invention comprises an insecticide carrier or insecticide, a method for making the same, and methods of using an insecticide formulation.

The insecticide carrier or insecticide of the invention comprises a mixture comprising petrolatum and diatomaceous earth. In the preferred embodiment, the insecticide carrier or insecticide comprises between approximately 5% and 25% by weight petrolatum and between approximately 5% and 90% by weight diatomaceous earth. The preferred embodiment may further comprise an insecticide containing an active ingredient between approximately 0.5% and 50% by weight insecticide, such as at least one member selected from the group consisting of *Bacillus Thuringiensis* (in the form of, for example, technical powder, PIPEL 2X ®, ABG-6203 ®, or DIPEL 8L ®), organophosphates (such as, for example, ORTHENE ®, parathion, or MALATHION ®), pyrethrum, pyrethroids, carbamates (such as, for example, SEVIN 80S ®), and a mixture of pyrethrum and piperonyl butoxide (between approximately 0.5% and 20% by weight piperonyl butoxide with respect to the total weight of the embodiment). The preferred embodiment may further comprise crop oil, such as a paraffinic crop oil such as, for example, CHEVRON BASE OIL C ® or SUN 11N ®, between approximately 25% and 85% by weight crop oil. The preferred embodiment may further comprise an emulsifier, such as, for example, TRITON X190 ®, between approximately 1% and 25% by weight emulsifier. The insecticide carrier or insecticide is preferably a spray.

The method of making an insecticide carrier or insecticide of the invention comprises the steps of mixing petrolatum and a crop oil and adding diatomaceous earth to the petrolatum/oil mixture. In the preferred embodiment, the step of mixing petrolatum and a crop oil comprises heating while mixing and the step of adding diatomaceous earth to the oil mixture comprises the further step of adding an insecticide containing an active ingredient. The step of mixing petrolatum and a crop oil may comprise the step of mixing white petrolatum and a paraffinic crop oil. The method may further comprise the steps of adding an emulsifier and formulating the resulting mixture into a spray. The step of mixing petrolatum and diatomaceous earth may comprise the steps of spraying petrolatum onto the diatomaceous earth and drying the resulting mixture to form a dust, and the additional step of formulating the dust into an oil spray formulation.

The first method of using an insecticide formulation of the invention comprises the steps of:

a) mixing petrolatum and a diluent;
b) adding diatomaceous earth to the petrolatum/diluent mixture; and
c) applying the resulting insecticide formulation to an appropriate surface. In the preferred embodiment, the step of mixing petrolatum and a diluent comprises heating while mixing, the step of applying the resulting formulation to an appropriate surface comprises the step of spraying the formulation onto vegetation, and the step of mixing petrolatum and a diluent comprises mixing petrolatum and a crop oil, such as, for example, white petrolatum and a paraffinic crop oil. The method may further comprise the step of adding an insecticide containing an active ingredient.

The second method of the invention of using an insecticide formulation comprises the steps of:

d) combining insecticide containing an active ingredient with petrolatum to form an insecticide-petrolatum mixture;
e) spraying the mixture onto diatomaceous earth;
f) drying the resulting mixture to a dust; and
g) applying the dust to an appropriate surface.

In the preferred embodiment, the step of combining insecticide with petrolatum comprises the step of combining a liquid insecticide with petrolatum and the step of applying the dust to an appropriate surface comprises spraying the dust onto vegetation. The method may comprise the additional steps of formulating the dust into an oil spray formulation and applying the oil spray formulation to an appropriate surface, such as vegetation.

The third method of the invention of using an insecticide formulation comprises the step of spraying the formulation onto vegetation, the formulation comprising a mixture of petrolatum, diatomaceous earth, and a diluent. In the preferred embodiment, the diluent in the formulation comprises a crop oil and the formulation further comprises an insecticide containing an active ingredient.

A primary object of the invention is to provide an insecticide carrier that is not itself phytotoxic and that extends the residual activity of an insecticide.

A further object of the invention is to provide an insecticide carrier that enhances insecticide effectiveness while resisting degradation.

Yet another object of the invention is the provision of an insecticide carrier which readily emulsifies yet retains effectiveness.

Still another object of the invention is the provision of an insecticide carrier and insecticide in a contact dust formulation that can be incorporated into spray formulations.

An advantage of the present invention is the formulation of an effective insecticide carrier and insecticide from inexpensive, inert constituents.

Yet another advantage of the present invention is its ease of formulation under field conditions.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DESCRIPTION OF THE PREFERRED EMBODIMENT
(BEST MODE FOR CARRYING OUT THE INVENTION)

The preferred insecticide carrier of the invention comprises a mixture of petrolatum (preferably white petrolatum), diatomaceous earth, and preferably a diluent, such as "crop oil." The carrier of the present invention provides increased wash-off resistance, increased effectiveness against insects, adhesion to vegetation, and ultraviolet shielding.

Crop oil is defined herein as inert petroleum agricultural spray oils which may be light to heavy paraffin oils preferably having viscosities ranging from 40 to 85 sec. Saybolt at 4° C. The preferred crop oils are non-phytotoxic. Examples of diluent crop oils include CHEVRON BASE OIL C ®, SUN 11N ®, and the like.

White petrolatum, in addition to providing increased viscosity, provides a screen against ultraviolet radiation. The white petrolatum further provides an encapsulation for the formulation, resisting the effects of oxidation and hydrolysis, thereby extending the active life of an insecticide. The white petrolatum further provides the formulation with an adhesive property for adhering to insects and vegetation when sprayed thereon.

The light absorbing properties of diatomaceous earth shield the insecticide from ultraviolet radiation. Furthermore, being abrasive, diatomaceous earth can puncture insect exoskeletons, thereby providing access for an insecticide. When ingested, diatomaceous earth lacerates internal organs, thereby also providing access for internal-acting poisons.

The carrier mixture is further preferably combined with an activeingredient insecticide. The insecticide may comprise powdered bacterials, such as *Bacillus Thuringiensis* technical powder, pyrethrum, pyrethroids, carbamates, and organophosphates, as well as other insecticides well known to those skilled in the art. Emulsifiers may also be used. The proportions of carrier components may be varied commensurately with the proportion of active ingredient in the insecticide to vary overall viscosity and to obtain any desired dilution ratio. The resulting formulations readily lend themselves to spray application.

The approximate preferred percentages by weight for each component are as follows: Petrolatum (5–25%), diatomaceous earth (5–90%), insecticide with active ingredient (0.5–50%), crop oil (25–85%), and emulsifier (1–25%).

Alternatively, liquid insecticides, such as *Bacillus Thuringiensis* (for example, DIPEL 8L ®), organophosphates, pyrethrum, or pyrethroids, may be combined with white petrolatum, using heat (preferably approximately 120° F.). This mixture is then sprayed in diatomaceous earth, and applied as a contact dust. If an oil spray formulation is desired, the contact dust may be further combined with a crop oil and applied as an oil spray.

EXAMPLES (INDUSTRIAL APPLICABILITY)

The following non-limiting examples illustrate several preparations of the insecticide carrier of the invention in combination with various insecticides. It is to be understood, however, that widespread variations and modifications may be employed to arrive at the composition of the invention.

EXAMPLE 1

White petrolatum was combined with a paraffinic crop oil in the preparation of 12–25% by weight petrolatum, using heat (approximately 120° F.). Powdered insecticides comprising organophosphates (for example, ORTHENE ®), pyrethrum, pyrethroids, *Bacillus Thuringiensis* (BT), carbamates and the like, and equal parts of diatomaceous earth were then blended into the prepared oil at a ratio of 30 grams active ingredient-diatomaceous earth to 100 grams of oil mixture.

Alteratively, after blending the heated paraffinic oil and petrolatum, one pound of diatomaceous earth was mixed with one gallon of the blended oil mixture.

Active ingredients were added in the following proportions:
1 pound of ORTHENE 75S ® per gallon of carrier;
up to 2 pounds of *Bacillus Thuringiensis* technical powder per gallon of carrier;
up to 2 pounds of SEVIN 80S ® per gallon of carrier.

Although considered most effective when free of emulsifiers, surfactants or wetting agents, the insecticide carrier can be used effectively with emulsifiers. The above formulation can be emulsified, for example, with TRITON X190® emulsifier, although other emulsifiers may be used. Such an emulsion has a representative viscosity of 525 cps, as opposed to 2,325 cps for the unemulsified formulation. Normally, 3-5% by weight of emulsifier was combined with the Example 1 formulation. Dilutions of over 50% result in decreased effectiveness.

EXAMPLE 2

White petrolatum was combined with CHEVRON BASE OIL C® in the proportions of 12-24% by weight petrolatum with the balance CHEVRON BASE OIL C®, using heat (120° F.). Powdered insecticide, such as *Bacillus Thuringiensis*, organophosphates (for example ORTHENE®) pyrethrum, pyrethroids, and carbamates were combined with equal parts of diatomaceous earth and then blended into the prepared oil at a rate of 30 grams active ingredient - diatomaceous earth to 100 grams of oil mixture.

Depending upon the actual insecticide, preparations varied slightly from those cited in the above example. Substitution of the more volatile CHEVRON® oil correspondingly permitted a greater proportion of petrolatum than in Example 1.

The Example 2 formulation set up more quickly than the Example 1 formulation, providing high resistance to wash-off in 2-3 hours.

Both the Example 1 and Example 2 mixtures provided spray formulations demonstrating resistance to wash-off, shielding from ultraviolet radiation, and resistance to hydrolysis and oxidation.

The following tables are taken from a report of tests of the insecticide carrier performed by the U.S. Department of Agriculture, Otis Methods Development Center, Otis Air National Guard Base, Massachusetts. The tests were performed under laboratory conditions, upon five tender oak seedlings, each exposed to 20 gypsy moth larvae (Lymantria dispor L).

The bacterial insecticides (*bacillus thuringiensis*) employed in these tests are the powder Dipel 2X by FMC (Farm Machinery Corporation), the powder ABG 6203 by Abbott Laboratories, and a liquid formulation, Dipel 8L, also by Abbott Laboratories. In these tests the bacterial insecticides were mixed with water, as they are normally used, and were compared to the same insecticide mixed with an emulsified insecticide carrier of the present invention and designated "Hen emul" in these reports.

Dipel 8L applied at 8BIU (billion international units) per acre is the most commonly used insecticide on gypsy moth. Tables 1 and 2 show a comparison of Dipel 8L in water at 1 to 16 BIU/gallon/acre to Dipel 8L at comparable rates in water and 64 oz./gallon/acre of the Henderson carrier. Table 3 shows Dipel 8L at 8 BIU/gallon/acre with the Henderson carrier used at rates of 64 oz./gallon down to 16 oz./gallon. Table 4 shows average percent larval mortality and seedling defoliation for a group of three tests conducted using ABG 6203 and Dipel 8L in water at 4 BIU/gallon/acre compared to the same rate of the toxicants in the Henderson carrier, Sun oil, and corn oil without water.

The results in this report illustrate the exceptional increase in efficacy using my formulation in various *bacillus thuringiensis* formulations at comparable BIU of the bacteria. This is especially evident in the comparative tests using low rates of toxicant as in Table 2.

Also of significance, this report shows no statistical difference in kill of larvae fed foliage treated with just my carrier compared with untreated foliage.

TABLE 1

Percent gypsy moth larval mortality and seedling defoliation following exposure to oak seedlings treated with Dipel 8L and "Henderson Carrier - Emulsified" - BT rates from 8 BIU to 16 BIU/gallon/acre

| Formulation | BIU/gal/acre | Percent mortality | | | Percent defoliation | | |
|---|---|---|---|---|---|---|---|
| | | 2 day | 4 day | 8 day | 2 day | 4 day | 8 day |
| 32 oz. 8L + 64 oz. "Hen Emul" + 32 oz. H2O | 16 | 46 | 84 | 95 | 3 | 8 | 13 |
| Dipel 8L + H2O | 16 | 14 | 48 | 79 | 10 | 17 | 41 |
| 28 oz. 8L + 64 oz. "Hen Emul" + 36 oz. H2O | 14 | 43 | 91 | 99 | 3 | 4 | 8 |
| Dipel 8L + H2O | 14 | 1 | 7 | 53 | 17 | 57 | 85 |
| 24 oz. 8L + 64 oz. "Hen Emul" + 40 oz. H2O | 12 | 43 | 85 | 99 | 2 | 4 | 5 |
| Dipel 8L + H2O | 12 | 1 | 7 | 67 | 12 | 42 | 72 |
| 20 oz. 8L + 64 oz. "Hen Emul" + 44 oz. H2O | 10 | 32 | 79 | 94 | 4 | 7 | 19 |
| Dipel 8L + H2O | 10 | 2 | 7 | 66 | 27 | 69 | 85 |
| 16 oz. 8L + 64 oz. "Hen Emul" + 48 oz. H2O | 8 | 31 | 75 | 96 | 3 | 6 | 13 |
| Dipel 8L + H2O | 8 | 0 | 9 | 41 | 15 | 62 | 98 |
| Control | — | 0 | 0 | 2 | 69 | 96 | 96 |

TABLE 2

Percent gypsy moth larval mortality and seedling defoliation following exposure to oak seedlings treated with Dipel 8L and "Henderson Carrier - Emulsified" - BT rates from 8 BIU to 6 BIU/gallon/acre

| Formulation | BIU/gal/acre | Percent mortality | | | Percent defoliation | | |
|---|---|---|---|---|---|---|---|
| | | 2 day | 4 day | 8 day | 2 day | 4 day | 8 day |
| 12 oz. 8L + 64 oz. "Hen Emul" + 52 oz. H2O | 6 | 19 | 87 | 92 | 3 | 17 | 18 |
| Dipel 8L + H2O | 6 | 1 | ·19 | 26 | 39 | 94 | 94 |
| 8 oz. 8L + 64 oz. "Hen Emul" + 56 oz. H2O | 4 | 9 | 67 | 83 | 5 | 31 | 41 |

TABLE 2-continued

Percent gypsy moth larval mortality and seedling defoliation
following exposure to oak seedlings treated with Dipel 8L
and "Henderson Carrier - Emulsified" - BT rates from
8 BIU to 6 BIU/gallon/acre

| Formulation | BIU/gal/acre | Percent mortality | | | Percent defoliation | | |
|---|---|---|---|---|---|---|---|
| | | 2 day | 4 day | 8 day | 2 day | 4 day | 8 day |
| Dipel 8L + H2O | 4 | 0 | 14 | 17 | 62 | 99 | 99 |
| 4 oz. 8L + 64 oz. "Hen Emul" + 60 oz. H2O | 2 | 5 | 49 | 62 | 13 | 66 | 69 |
| Dipel 8L + H2O | 2 | 0 | 17 | 24 | 64 | 96 | 96 |
| 2 oz. 8L + 64 oz. "Hen Emul" + 62 oz. H2O | 1 | 5 | 45 | 58 | 15 | 87 | 88 |
| Dipel 8L + H2O | 1 | 0 | 5 | 5 | 82 | 96 | 96 |
| Control | — | 0 | 3 | 3 | 81 | 92 | 92 |

TABLE 3

Percent gypsy moth larval mortality and seedling defoliation
following exposure to oak seedlings treated with Dipel 8L
and various amounts of "Henderson Carrier- Emulsified" at
8 BIU/gallon/acre

| Formulation | Percent mortality | | | Percent defoliation | | |
|---|---|---|---|---|---|---|
| | 2 day | 4 day | 8 day | 2 day | 4 day | 8 day |
| 16 oz. 8L + 64 oz. "Hen Emul" + 48 oz. H2O | 35 | 92 | 100 | 3 | 4 | 5 |
| 16 oz. 8L + 56 oz. "Hen Emul" + 56 oz. H2O | 41 | 84 | 99 | 3 | 4 | 8 |
| 16 oz. 8L + 48 oz. "Hen Emul" + 64 oz. H2O | 44 | 70 | 100 | 3 | 3 | 4 |
| 16 oz. 8L + 40 oz. "Hen Emul" + 72 oz. H2O | 19 | 61 | 87 | 3 | 22 | 24 |
| 16 oz. 8L + 32 oz. "Hen Emul" + 80 oz. H2O | 14 | 38 | 94 | 10 | 29 | 48 |
| 16 oz. 8L + 30 oz. "Hen Emul" + 82 oz. H2O | 3 | 32 | 80 | 16 | 24 | 39 |
| 16 oz. 8L + 26 oz. "Hen Emul" + 86 oz. H2O | 0 | 16 | 53 | 32 | 52 | 72 |
| 16 oz. 8L + 22 oz. "Hen Emul" + 90 oz. H2O | 1 | 23 | 72 | 24 | 33 | 54 |
| 16 oz. 8L + 16 oz. "Hen Emul" + 96 oz. H2O | 1 | 19 | 53 | 32 | 47 | 59 |
| Control | 0 | 0 | 1 | 39 | 94 | 94 |

TABLE 4

Average percent larval mortality and seedling defoliation
for a series of three tests using BT at 4 BIU/gallon/acre

| Formulation | Percent mortality | | | Percent defoliation | | |
|---|---|---|---|---|---|---|
| | 2 day | 4 day | 8 day | 2 day | 4 day | 8 day |
| ABG-6203 + H2O | 1 | 7 | 39 | 32 | 72 | 79 |
| ABG-6203 + "Hen Emul" | 44 | 81 | 98 | 3 | 6 | 7 |
| ABG-6203 + Sun Oil | 39 | 69 | 92 | 6 | 10 | 21 |
| ABG-6203 + Corn Oil | 22 | 49 | 81 | 10 | 25 | 39 |
| Dipel 8L + H2O | 0 | 2 | 29 | 45 | 79 | 82 |
| Dipel 8L + "Hen Emul" | 40 | 74 | 98 | 3 | 6 | 7 |
| Dipel 8L + Corn Oil | 36 | 58 | 88 | 9 | 19 | 26 |
| Dipel 8L + Sun Oil | 14 | 33 | 87 | 11 | 19 | 33 |
| Control | 0 | 0 | | 68 | 92* | |
| Control ("Hen Emul") | 0 | 2 | | 70 | 94* | |
| Control (Corn Oil) | 0 | 2 | | 68 | 97* | |
| Control (Sun Oil) | 0 | 1 | | 74 | 95* | |

*Test insects changed to artificial diet

As can be seen from the above test results and tables, the insecticide retains potency over a longer time period and defoliation is correspondingly reduced using the insecticide carrier of the present invention ("Hen Emul").

EXAMPLE 3

Liquid insecticides comprising up to 2% by weight active ingredients, such as *Bacillus Thuringiensis* (for example, Dipel 8L), organophosphates, pyrethrum or pyrethroids, were combined with 10% by weight of white petrolatum using heat (120 deg. F.). This mixture was then sprayed with a ribbon blender onto and absorbed by diatomaceous earth and dried.

When pyrethrum was used as the active ingredient, the pyrethrum was first combined with pipernoyl butoxide in the proportion of 6 parts pyrethrum to 1 part piperonyl butoxide prior to combination with petrolatum. Piperonyl butoxide synergistically enhances the pyrethrum.

The resulting dusts provided effective and long lasting toxicity as contact insecticides. The above dusts were also formulated into oil spray formulations. Petrolatum (10 to 12% by weight) was combined with SUN 11N® or CHEVRON BASE OIL C® using heat (approximately 120° F.). The Example 3 dusts were then combined with this petrolatum - oil at a rate of 30 grams dust to 100 grams of petrolatum - oil. This oil spray formulation provided extended protection against insects equivalent to that produced by the Example 1 and Example 2 formulations.

EXAMPLE 4

Pyrethrum (160 grams, 50% by weight) was combined with 477 grams of piperonyl butoxide. This mixture was emulsified with 160 grams of TRITON X190 ® emulsifier. The resulting mixture was combined with 454 grams of diatomaceous earth.

Petrolatum (193 grams) was combined with 1736 grams of Sun 11N oil or the equivalent, using heat. The resulting oil was then blended with the active ingredient/diatomaceous earth mixture.

This formulation produced a home garden spray which was diluted with water at a rate of 1 to 4 ounces formulation per gallon of water. Excellent results were attained with this spray and found to be particularly effective against scale insects, aphids, wasps, and the like.

EXAMPLE 5

Pyrethrum (160 grams, 50% by weight) was mixed with 476 grams of piperonyl butoxide. This mixture was in turn mixed with 454 grams of diatomaceous earth. Petrolatum (250 grams), using heat, was combined with 1,836 grams of CHEVRON BASE OIL C ® or equivalent. The active ingredient/diatomaceous earth mixture was blended with this oil.

The resulting oil formulation provided a broad spectrum agricultural insecticide, especially effective for crops. As noted previously, the carrier of the present invention provides increased wash-off resistance, increased effectiveness against scale insects, adhesion to vegetation, and ultraviolet shielding.

EXAMPLE 6

MALATHION ® (1,360 grams, 91% by weight) was mixed with 34 grams of TRITON X190 ® emulsifier or the equivalent. This mixture was in turn combined with 454 grams of diatomaceous earth. Using heat, 186 grams of petrolatum were combined with 1,557 grams of SUN 11N ® or CHEVRON BASE OIL C ® or the equivalent, and blended with the active ingredient/diatomaceous earth mixture.

The Example 6 formulation provided grasshopper control and was also especially effective as an undiluted spray against adult mosquitoes.

Although the invention has been described with reference to these preferred embodiments, other embodiments can achieve the same results. Variations and modifications of the present invention will be obvious to those skilled in the art and it is intended to cover in the appended claims all such modifications and equivalents.

What is claimed is:

1. An insecticidal composition comprising an insecticidally effective amount of an insecticide selected from the group consisting of *Bacillus thuringiensis*, pyrethrum and a mixture of pyrethrum and pipernoyl butoxide, in combination with an insecticidal activity extending amount of semi-solid petrolatum and diatomaceous earth.

2. The composition of claim 1, in the form of a wettable powder, which further comprises an emulsifier.

3. The composition of claim 1, in the form of an emulsifiable concentrate, which further comprises a nonphytotoxic paraffinic crop oil and an emulsifier.

4. A method of controlling insects which comprises applying an insecticidally effective amount of the composition of claim 1 to vegetation.

5. A method of controlling insects which comprises applying an insecticidally effective amount of the composition of claim 2 to vegetation.

6. A method of controlling insects which comprises applying an insecticidally effective amount of the composition of claim 3 to vegetation.

7. The method of claim 6 wherein the method of applying comprises spraying.

* * * * *